United States Patent [19]

Chiesi et al.

[11] Patent Number: 4,942,167

[45] Date of Patent: Jul. 17, 1990

[54] PHARMACEUTICAL COMPOSITIONS OF PIROXICAM IN AQUEOUS SOLUTIONS AND PROCESS FOR THEIR PREPARATION

[75] Inventors: Paolo Chiesi; Luciana Pavesi, both of Parma, Italy

[73] Assignee: Chiesi Farmaceutici S.p.A., Parma, Italy

[21] Appl. No.: 331,457

[22] Filed: Mar. 31, 1989

[30] Foreign Application Priority Data

Apr. 1, 1988 [IT] Italy ............................. 20073 A/88

[51] Int. Cl.$^5$ ............................................. A61K 31/54
[52] U.S. Cl. ............................... 514/226.5; 514/224.2
[58] Field of Search ........................... 514/226.5, 224.2

[56] References Cited

PUBLICATIONS

Derwent Abst. C84-125216.

*Primary Examiner*—Douglas W. Robinson
*Assistant Examiner*—Zohreh A. Fay
*Attorney, Agent, or Firm*—Bucknam and Archer

[57] ABSTRACT

Aqueous pharmaceutical formulations containing the active principle piroxicam or N-(2-pyridyl)-2-methyl-4-hydroxy-2H-1,2-benzothiazine-3-carboxyamido-1,1-dioxide, are described.

The compositions of the invention are particularly suited for the injectable use, both because of their tolerability degree and for the favorable pharmacokinetics profile and may be advantageously used also for the preparation of collyria or eye-washes.

7 Claims, No Drawings

PHARMACEUTICAL COMPOSITIONS OF PIROXICAM IN AQUEOUS SOLUTIONS AND PROCESS FOR THEIR PREPARATION

The present invention refers to pharmaceutical compositions of piroxicam in aqueous solutions, particularly suited for the preparation of injectable compositions.

Piroxicam, whose chemical name is N-(2-pyridyl)-2-methyl-4-hydroxy-2H-1,2-benzothiazine-3-carboxyamido-1,1-dioxide, is a nonsteroidal antiinflammatory drug widely used in the treatment of arthro-rheumatic diseases; for these indications, it is normally administered by the oral or rectal route.

Piroxicam is, on the other side, endowed with a remarkable analgesic activity and therefore it is effectively used also in the treatment of pain both associated with arthro-rheumatic diseases and of different kind (cephalea, dysmennorrhea, painful manifestations of different kind).

When the desired therapeutic effect is mainly the analgesic one, it is particulary useful to make available compositions for parenteral use allowing more rapid hematic levels of active principle and consequently a rapid alleviation of pain. The poor water-solubility of piroxicam does not allow the formulation thereof in aqueous solutions suited for the preparation of injectable compositions.

In order to cope with this drawback, several proposal have been made.

The European Patent No. 66458 discloses piroxicam salts with arginine and lysine, which may be used for the preparation of compositions for parenteral use.

Analogously, the European Patent No. 66459 discloses piroxicam salts with ethylenediamine, monoethanolamine and diethanolamine.

EP-A-177870 discloses aqueous-organic solutions of piroxicam, consisting of 50% water, 40% ethanol to which sub-stoichiometric amounts of N-methylglucamine are added as stabilizer of the solution.

It has now been found a piroxicam composition for parenteral use wherein the active principle is present as alkaline or alkali-earth metal salt and preferably as sodium salt, dissolved in water for injectable preparations.

This formulation, which may also be used for the preparation of collyria or eye-washes, besides to the preparation of injectable solutions for intramuscular, intravenous or intraarticular use, has the following advantages in comparison with the known compositions:
1. easy preparation, because the process allow to obtain the final formulation by few and simple steps, without the isolation and crystallization of salts of the active principle;
2. total absence of cosolvents such as alcohols or glycols which may give rise to general or local tolerability problems;
3. as a consequence of what above said in item 2, a better respect of the physiological conditions and consequently a particularly high tolerability;
4. a better pharmacokinetic behaviour, mainly as far as the maximal values of plasmatic concentrations ($C_{max}$) are concerned, in comparison to a commercial piroxicam injectable preparation.

A second object of the invention is provided by the process for the preparation of aqueous solutions of piroxicam, consisting in the dispersion in water of the active principle in concentrations ranging from 1 to 4% w/v and subsequent addition, under stirring, of an aqueous solution of alkaline or alkali-earth hydroxide, preferably 1N sodium hydroxide in stoichiometric amount up to complete dissolution. The present invention provides pharmaceutical composition for injectable use, containing from 10 to 30 mg of active principle per dosage unit, in form of ready-to-use solution or in lyophilized form to be dissolved in water for injection before use. The present invention also provides compositions for ophthalmic use in which concentration of the active principle is from 0.2 to 1%.

Glycine is added to said solution in amounts ranging from 8–10% w/v as pH-stabilizer.

The so obtained final solution may be subdivided in vials and subsequently sterilized in autoclave or alternatively it may be sterilized by filtration and then dosed in vials and lyophilized in sterile room. The lyophilized may be easily re-dissolved in water for injectable preparations, just prior to the use, giving a clear aqueous solution.

The latter preparation is preferred since the active principle, in form of lyophilized powder, keeps its chemical stability unchanged during time.

The following examples illustrate but do not limit the invention anyhow.

EXAMPLE 1: PREPARATION OF THE LYOPHILIZED

| Composition of a lyophilized vial: | |
| --- | --- |
| Piroxicam | mg 20 |
| Sodium hydroxide 1N | ml 0,12 |
| Glycine | mg 100 |
| Water for injection | q.s. to 1 ml |

Preparation method

Piroxicam is dispersed in water, the aqueous solution of sodium hydroxide is added so as to obtain a clear solution.

The glycine is added and the solution is stirred till it becomes clear.

The solution is then sterile-filtered through a 0.2 μm membrane.

The subsequent operations of distribution, lyophilization and vial sealing are carried out in sterile room by known and standardized methods.

The lyophilized, prior to its use, is dissolved in 2 ml of water for injection yielding a clear solution having pH=8–8.5.

EXAMPLE 2: PREPARATION OF THE READY-TO-USE SOLUTION

Injectable piroxicam compositions as ready-to-use solutions are prepared as in Example 1.

The solution may conveniently contain benzyl alcohol as a conservative and local anesthetic agent.

Two different composition are reported:

| Composition (a) | |
| --- | --- |
| Piroxicam | mg 20 |
| Sodium hydroxide 1N | ml 0.172 |
| Glycine | mg 80 |
| Water for injection | q.s. to 2 ml |
| Composition (b) | |
| Piroxicam | mg 20 |
| Sodium hydroxide 1N | ml 0.172 |
| Glycine | mg 80 |
| Benzyl alcohol | mg 20 |

-continued

| Water for injection | q.s. to 2 ml |

The sterilization may be carried out by filtration through a 0.2 μm membrane and subsequent distribution in vials in sterile room. Alternatively, the sterilization may be carried out by heating in autoclave after distribution of the solution in vials.

Said aqueous solutions of piroxicam may also be used in the preparation of collyria, optionally adding to the composition antibacterial compounds, such as quaternary ammonium salts.

The kinetic behavior of the pharmaceutical composition of the invention has been evaluated in man in comparison with a standard, commercially available injectable formulations whose composition is the following:

| Piroxicam | mg 20 |
| Benzyl alcohol | mg 20 |
| Nicotinamide | mg 30 |
| Propylene glycol | mg 400 |
| Water for injection | ml 1 |

The study was carried out on 6 adult healthy volunteers, according to a cross-over design using the injectable composition of Example 1, hereinafter referred to as CHF 1251.

Both the reference composition and that of the present invention, comprised 20 mg of active principle. The administration was carried out by the intramuscular route. The determination of the plasma concentration of the active principle at different times from administration was carried out by high pressure liquid chromatography (HPLC).

The results obtained expressed as mean values of the plasma concentrations at different times, AUC (area under the curve blood concentration/time), MRT (mean residence time), $C_{max}$ (maximum plasma concentration) and $T_{max}$ (time needed for reaching the maximum plasma concentration) are reported in table 1.

composition, whose mean max. concentration was 2.20 μg/ml achieved after a mean time of 3.58 h after treatment.

The plasmatic profile of CHF 1251 shows moreover that the drug remains in the plasma compartment for a long time, as it is evident from MRT values ranging from 43 to 74 hours (mean value: 60 hours and 20 minutes).

The permanence time of piroxicam in plasma after CHF 1251 administration is longer than that obtained with the commercial injectable formulation of piroxicam, showing a mean value of about 54 hours and 30 minutes.

According to the results obtained in this comparative study, using as a reference drug a commercial, standard injectable preparation of piroxicam, it can be concluded that the composition of the invention has a particularly favourable plasma pharmacokinetics profile, characterized by a fast absorption and above all by the achievement of a significantly higher maximum plasma concentration (about 5% higher) than that obtained with the reference formulation.

This result is particularly important for the desired therapeutic effect of a fast and effective analgesic action.

In fact, the treatment by parenteral route is used in cases of acute pain of remarkable seriousness just for the faster rapidity of the antalgic effect.

In the case of non-steroidal antiphlogistic drugs, clinically used for the treatment of acute pain of different etiology, the parenteral administration is generally better tolerated in comparison with the oral route as far as undesired side-effects at the gastro-intestinal tract level are concerned and it is preferably used for patients affected by gastro-intestinal diseases.

In addition to a better general tolerability in comparison to the oral route, the composition of the invention has also a better local tolerability in comparison with the commercial, standard injectable formulation, already used for the kinetics study.

Most of the non-steroidal anti-inflammatory drugs

TABLE 1

Plasma kinetics of piroxicam in man (healthy volunteers) after intramuscular administration of 20 mg of active principle from the composition of the invention (CHF 1251) and from a standard commercially available composition.

| Compositions | No. subjects | | Meanvalue and standard deviating (X, ± SD) of plasma conc. of (μg/ml) of piroxicam at different times (h) after administration | | | | | | | AUC h · μg/ml | MRT h | $C_{max}$ μg/ml | $T_{max}$ h |
| --- | --- | --- | --- | --- | --- | --- | --- | --- | --- | --- | --- | --- | --- |
| | | | 0.25 | 0.50 | 1 | 2 | 4 | 8 | 24 | | | | |
| CHF 1251 | 6 | X ± | 2.38 | 2.43 | 2.43 | 2.02 | 1.73 | 1.79 | 1.26 | 115.28 | 60.20 | 2.61 | 1.58 |
| | | D.S. | 0.23 | 0.48 | 0.51 | 0.37 | 0.42 | 0.46 | 0.41 | 29.02 | 11.29 | 0.39 | 2.18 |
| Commercial injectable piroxicam | 6 | X ± | 0.98 | 1.57 | 1.89 | 1.69 | 1.92 | 1.78 | 1.35 | 150.63 | 54.29 | 2.20 | 3.58 |
| | | D.S. | 0.32 | 0.52 | 0.34 | 0.30 | 0.53 | 0.54 | 0.44 | 71.35 | 29.52 | 0.33 | 2.38 |

The AUC and $C_{max}$ values were compared by the variance analysis method as disclosed by Wagner J. G. on Fundamental of Clinical Pharmacokinetics, Hamilton 3°, Drug Intell. Publ. 291–4, 1975.

The $T_{max}$ values were compared by the non-parametric Wilcoxon test as disclosed by Siegel S. on "Statistica non parametrica per le scienze del comportamento", Ed. OS, Firenze 63–70, 1966.

As it can be shown from the data reported in Table 1, the absorption is very fast after administration of the injectable piroxicam formulation CHF 1251: the blood concentration peak is ranging from 2.14 to 3.14 μg/ml (mean value 2.61 μg/ml) and it is achieved after a mean time of 1.58 h after treatment whereas the commercial usually administered by intramuscular route as well as other active principles are badly tolerated locally since they are endowed with an histolesive action causing the release of neurohumors and of intracellular proteolytic enzymes, with consequent local intolerability manifestations such as burning, pain, reddening and induration at the injection site.

One of the quantitative evaluation methods of the tissue damage is the determination of the serum level of an enzyme characteristics of the muscular fibre, the creatine phophokinase (CPK), normally present in blood in low concentrations (up to 250 mU/ml), which may however considerably increase with few hours in case of myolysis and cellular necrosis due to causes of different nature such as the administration of drugs by the intramuscular route.

The administration of serum level of CPK represents therefore a convenient biochemical test whenever the local tolerability of any injectable preparation for intramuscular use should be evaluated (Cingolani E. et al. Il Farmaco Ed. Pr. 41(3), 89, 1986).

The evaluation of the local tolerability of the composition of the invention has been carried out by measuring the serum levels of CPK and the direct detection of intolerability symptoms and signs at the injection site, in 6 healthy volunteers which were considered suited according to a series of exam and were subjected to a treatment cycle with 6 vials of CHF 1251 (2 vials at 8 hours interval at the first day and 1 vial/day for the subsequent 4 days).

The tolerability of the reference drug, i.e. of the commercial injectable formulation of piroxicam was evaluated by the same method and at the same time.

The results of the serum CPK levels at different times are shown in Table 2.

This objective evaluation of the local tolerability of the compositon of the invention has been further confirmed by the subjective evaluation of volunteers who only in some cases complained about burning reactions at the injection site.

I claim:

1. A process for the preparation of an aqueous pharmaceutical composition containing as active ingredient a basic salt of piroxicam which consists of (a) dispersing piroxicam in water in a concentration between 1 and 4% w/v; (b) adding under stirring an aqueous solution of an alkali or alkaline earth metal hydroxide in stoichiometric amount up to complete dissolution; (c) adding glycine in an amount between 8 and 10% w/v as a pH stabilizer and stirring to obtain a ready to use solution.

2. The process according to claim 1 wherein said solution is sterilized after step (c).

3. The process according to claim 2 wherein said solution is lyophilized after having been sterilized.

4. The process according to claim 1 wherein said alkali metal hydroxide is sodium hydroxide.

5. A pharmaceutical composition of piroxicam in

TABLE 2

Meanvalues and standard deviation of plasma CPK (mU/ml) at different times during a treatment cycle respectively of CHF 1251 and of commercial injectable formulation of piroxicam.

| DRUG | No. subjects | | 0 | 1 | 2 | 3 | 4 | 5 | 6 | 7 | 8 | 9 | 10 | 11 | 12 |
|---|---|---|---|---|---|---|---|---|---|---|---|---|---|---|---|
| CHF 1251 | 6 | $\bar{X}$ | 81.2 | 77.0 | 79.5 | 95.7 | 98.8 | 100.5 | 94.0 | 98.7 | 103.3 | 114.2 | 106.8 | 93.7 | 81.3 |
|  |  | D.S. | 6.0 | 20.4 | 19.7 | 18.5 | 21.4 | 34.7 | 12.4 | 27.5 | 22.8 | 27.0 | 18.8 | 19.2 | 12.6 |
| commercial injectable piroxicam | 6 | $\bar{X}$ |  | 135.3 | 140.0 | 168.7 | 191.5 | 306.3 | 334.5 | 196.3 | 201.8 | 220.2 | 234.5 | 242.2 | 198.5 |
|  |  | D.S. |  | 47.9 | 47.0 | 40.4 | 59.7 | 140.1 | 164.3 | 73.0 | 71.1 | 99.2 | 110.2 | 103.4 | 89.8 |

Before test start: 0 = basal
During test:
1 = day 1, time 0
2 = day 1, time 20'
3 = day 1, time 7 hours
4 = day 1 (second injection), time 2 h
5 = day 3, time 20'
6 = day 3, time 7 hours
7 = day 5, time 0
8 = day 5, time 20'
9 = day 5, time 2 hours
10 = day 5, time 3 hours
11 = day 5, time 7 hours
12 = day 6, time 0

As it can be noticed from the data of table 2, the histolesive effect is completely lacking with CHF 1251 whereas it is present, although in modest amount, with the reference formulation.

Since the two formulations comprise the same active principle, said effect is probably due to the solvent's action (a mixture of propylene glycol-benzyl alcohol-water) of the commercial product.

CHF 1251 using a purely aqueous carrier did not induce any tissue damage detectable by the used tests.

aqueous solution for injectable use prepared according to the process of claim 1 containing from 10 to 30 mg of piroxicam per dosage unit.

6. A pharmaceutical composition according to claim 5 for ophthalmic use, wherein the concentration of piroxicam is from 0.2 to 1%.

7. A pharmaceutical composition prepared by the process of claim 3 which is stored in the lyophilized form.

* * * * *